Figure 1:
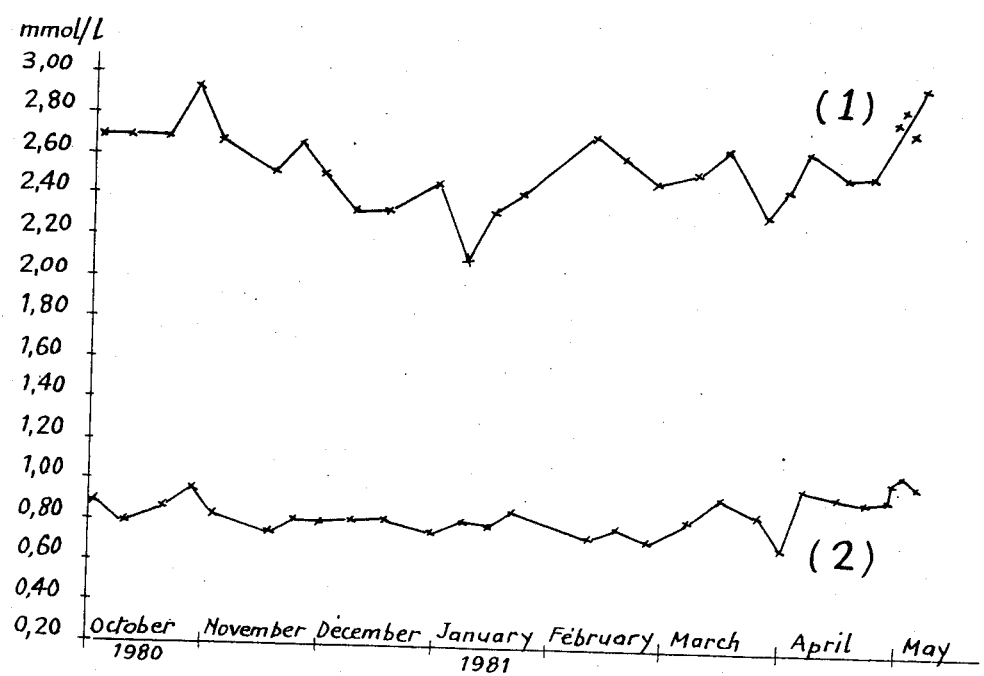

United States Patent [19]

Collery

[11] Patent Number: 4,596,710
[45] Date of Patent: Jun. 24, 1986

[54] GALLIUM CHLORIDE AS A NEW ANTI-CANCEROUS DRUG

[75] Inventor: Philippe Collery, Ay, France

[73] Assignee: Les Laboratoires Meram, Paris, France

[21] Appl. No.: 609,329

[22] Filed: May 11, 1984

Related U.S. Application Data

[63] Continuation of Ser. No. 344,793, Feb. 1, 1982, abandoned.

[30] Foreign Application Priority Data

Feb. 20, 1981 [FR] France ............................... 81 03355

[51] Int. Cl.$^4$ ............................................. A61K 33/24
[52] U.S. Cl. .................................................. 424/131
[58] Field of Search ......................................... 424/131

[56] References Cited

PUBLICATIONS

Villini, Chem. Abst., 61: 6252(a) (1963).
Collery, Trace Substances in Environmental Health–XV, pp. 208–216 (1981).
Adamson, Cancer Chemother. Rep., Part 1, 59, pp. 599–610 (1975).
Anghileri, Arzneimittel-Forschung, 25, pp. 793–795 (1975).
Hart, Proc. Nat. Acad. Sci., U.S., 68, pp. 1623–1626 (1971).
Collery, Magnesium–Bull., 3, pp. 23–25 (1981).

*Primary Examiner*—Michael L. Shippen
*Attorney, Agent, or Firm*—Morgan, Finnegan, Pine, Foley and Lee

[57] ABSTRACT

The present invention relates to the application of gallium chloride as drug particularly useful for the treatment of malignant tumors, and to the pharmaceutical compositions particularly intended for oral administration and containing from 100 to 500 mg of active ingredient per unit dose.

2 Claims, 3 Drawing Figures

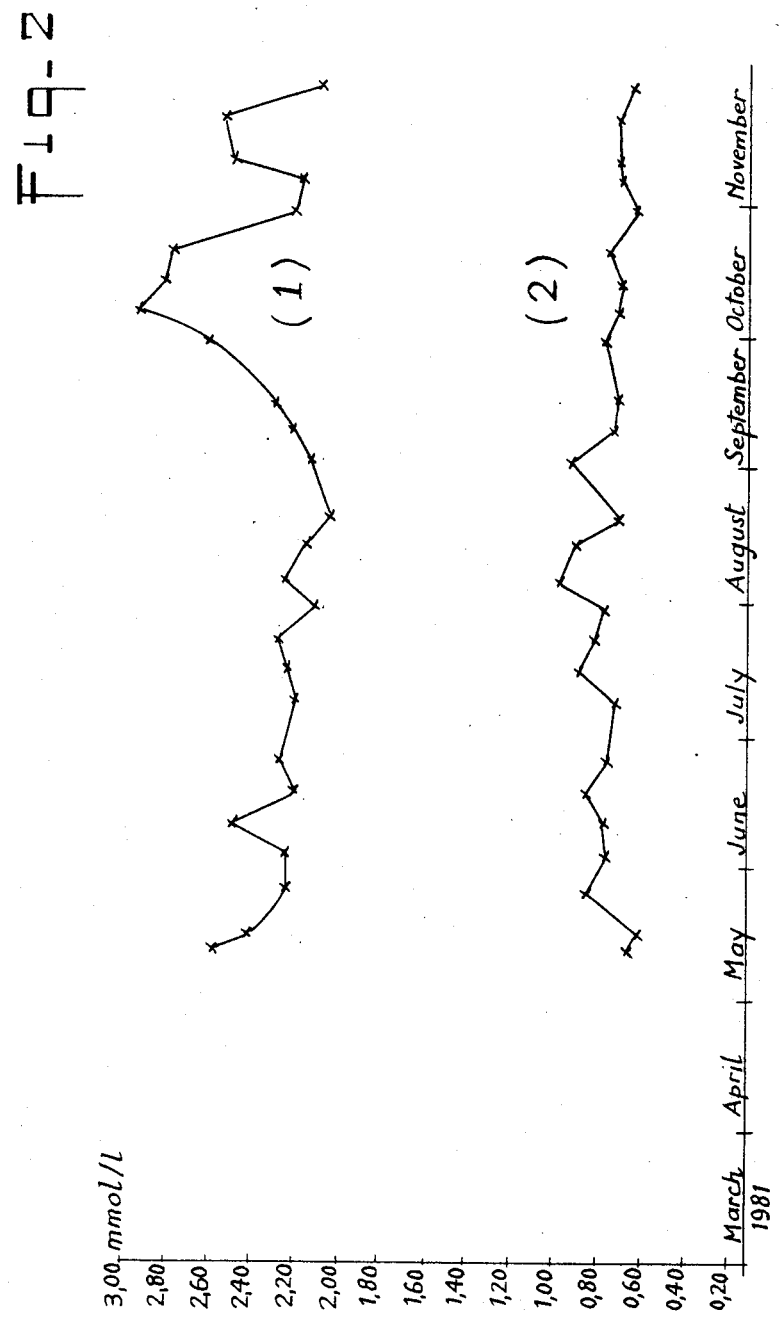

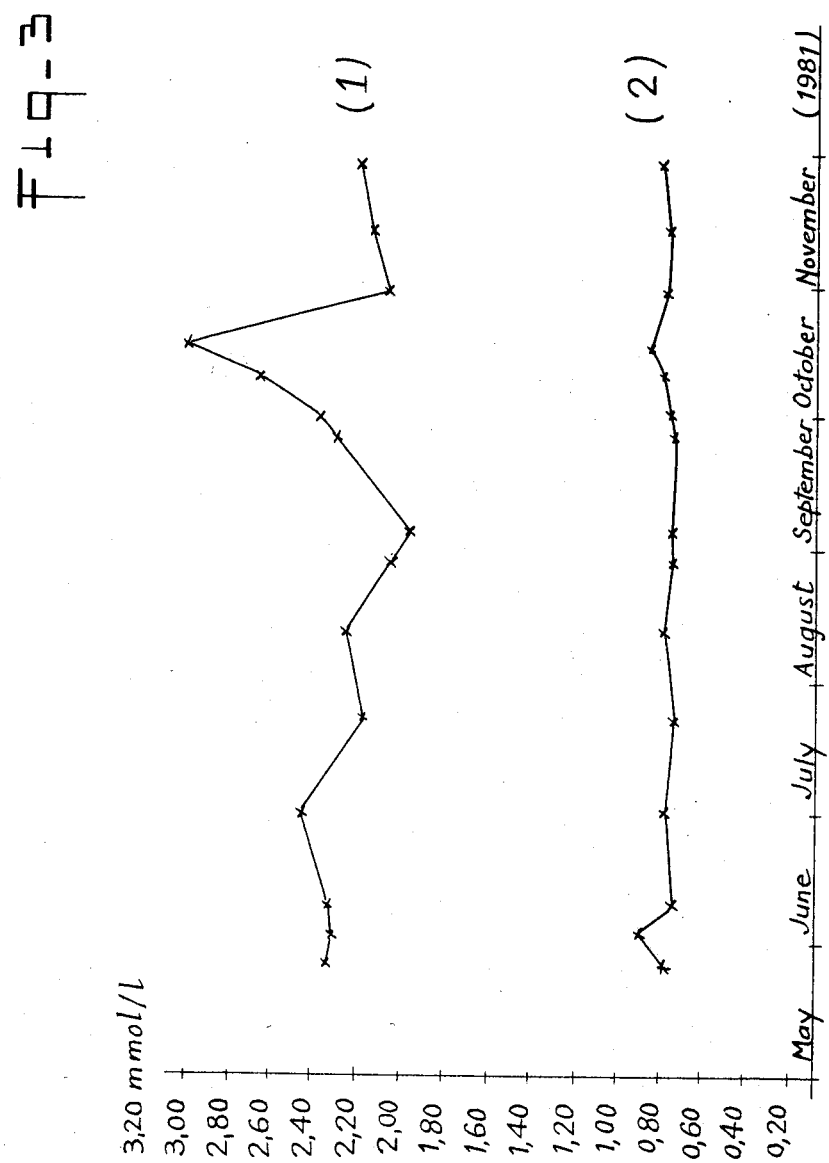

GALLIUM CHLORIDE AS A NEW ANTI-CANCEROUS DRUG

This is a continuation of application Ser. No. 344,793 filed Feb. 1, 1982, now abandoned.

The present invention relates to the use of gallium chloride, of formula GaCl₃ as drug for the treatment of malignant tumours.

Magnesium is known to be necessary for tumoral growth and the concentration of magnesium is high in malignant tumours. To slow down tumoral growth, an inhibitor would therefore be necessary which is competitive with the magnesium and would take its place in the malignant cell without fulfilling its function. It has already been observed that gallium was capable of displacing magnesium from the cell (Anghileri L. J., Strahlentherapie 1973, 146, 359–366). Certain authors have also reported that the gallium salts might have an anti-tumoral activity in animals, but this activity was not found again later and tests using gallium nitrate in human therapeutics were not continued due to the minor results observed and the excessive renal toxicity of the product.

It has been found, according to the invention, that gallium chloride may be used with good results and without major drawbacks, in the treatment of malignant tumours in humans.

The anti-tumoral effect of gallium chloride was firstly studied in female dogs having spontaneous malignant tumours of the breast. Gallium chloride therapy was carried out in bitches having a mammary cancer (tubulo-pillary adenocarcinoma or mixed-type tumour); treatment started either at the stage of the primary tumour (4 bitches) or upon a recurrence after a surgical excision (10 bitches).

The gallium chloride was administered in the form of drinkable ampoules containing 1 mg or 10 mg per ml of active product, at a dose of 1 mg/kg in the first bitches; this dose was rapidly increased to 5 mg/kg as soon as tolerance proved to be good, particularly from the digestive point of view, and the duration of treatment was two months.

The results were as follows:

(1) In the 4 bitches treated at the primary tumour stage, the following was observed:
one death on the 7th day in one case;
a regression of the tumour in the other three cases.

In two cases, the treatment was continued for two months, the tumour reducing from 10×7 cm to 8.5×7 cm in one case and from 1.5×1.3 to 1.5×1.0 cm in the other case.

In the third case, the treatment could be continued for more than six months in a very old bitch of 14 years. For two months, the posology was 5 mg/kg, then treatment was stopped for one month due to a dyspnoea then resumed at the posology of 2.5 mg/kg for three and a half months, reduced to 1 mg/kg the following month. The tumour, which had doubled in size during the four months preceding the treatment, and which reached the size of 3.6×2 cm, did not develop during the first two months of treatment, increased a gain during the month without treatment, and regressed after resumption of the treatment (3×2 cm) and become very hard.

(2) In the 10 bitches treated at the recurrence stage, the following was observed:
one death in the third week of treatment, due to a pulmonary metastasis;

three complete remissions after two months of treatment, in bitches which had a recurrent tumour which, at the beginning of the treatment, was smaller than 0.6 cm in diameter;
in 5 bitches, a partial regression of the tumour with hardening thereof after three months of treatment.

The biopsies made at the end of the treatment showed that tumoral cells persisted, but a histological study suggested an increase in the amorphous ground substance with a cellular rarefaction;
persistent growth of the tumour in one bitch treated with 1 mg/kg of gallium chloride for one month, which posology was increased to 2.5 mg/kg for the following fifteen days, then to 5 mg/kg for the last fifteen days.

The efficacity of the gallium chloride therapy can appear only after several months of treatment. This was what was observed during the treatment of two bitches suffering from mammary tumours which were initially very evolutive (as, for these two dogs, this was a third recurrence which normally led to death very quickly, in a few weeks).

Observation of first bitch (OUD . . . )

Posology of gallium chloride, per os: 7.5 mg/kg from 15.4.1981 to 14.9.1981, then 10 mg/kg.
Histology of this third recurrence: adenocarcinoma (diagnosis by needle-biopsy)
Size of the tumour:
  5.0 cm in diameter on 4.15.1981
  5.5×8.5 cm in diameter on 5.26.1981
  5.5×8.5 cm in diameter on 6.25.1981
  6.5×9.5 cm in diameter on 9.14.1981
  9.5×10 cm in diameter on 10.14.1981,
then tumoral stabilisation up to Dec. 28th, 1981 when the dog suddenly died (good general state during the preceding days) of a myocardial infarction with acute oedema of the lung and overall heart failure.
At the autopsy: no hepatic nor pulmonary metastases a small nodule of 1 cm in the spleen.
Clinical and renal tolerance: perfect.

Observation of second bitch (BEL . . . )

Posology of gallium chloride per os: 2.5 mg/kg from 27.2.1981 to 30.4.1981, then 5 mg/kg up to 11.3.1981, then 7 mg/kg.
Histology (as for first bitch OUD . . . )
Size of the tumour:
  1.2 cm in diameter on 2.27.1981
  1.8 cm in diameter on 4.1.1981
  2.3 cm in diameter on 4.30.1981
  3.0×2.5 cm in diameter on 5.25.1981
  4.8×3.5 cm in diameter on 7.2.1981
  5.2×4.2 cm in diameter on 7.30.1981
  6.0×4.5 cm in diameter on 9.1.1981
then the growth clearly slowed down with an obvious change in the consistency of the tumour.
Nevertheless, the tumour continued to progress:
  6×4.5 cm in diameter on 4.10.1981
  7×5.5 cm in diameter on 3.11.1981
  8×6.0 cm in diameter on 3.12.1981
  8×6.0 cm in diameter on 6.1.1982,
on which date surgical excision of this tumour, which had virtually not enlarged since Nov. 3rd, 1981, was carried out.
Upon opening of the excised piece: considerable necrosis occupying virtually all the tumour.
Clinical and renal tolerance: perfect.

Pulmonary radiograph of 5.1.1982: normal.

Gallium chloride at a dose of 5 mg/kg therefore gave good results in the treatment of mammary tumours in the bitch, provided that the duration of the treatment could be extended. Clinical and biological tolerance is excellent. Regression of the tumour remains weak and seems rathermore to be a retraction of the tumour which becomes very hard and appears like a stone, at excision. Surgical treatment at this stage appears to be recommended. Due to this therapeutic strategy, seven out of eight bitches are alive and the survival time is now significant.

Acute toxicity of gallium chloride was studied on the mouse: the $LD_{50}$ per os is equal to 10.1 mmoles/kg (or 1790 mg/kg) with a fiducial limit of between 8.2 and 12.5 mmoles/kg (or between 1450 and 2209 mg/kg) for p=0.05.

As mammary tumours in the female dog constitute an excellent experimental model, and as the results are reproducible in humans, clinical experiments were carried out in patients suffering from advanced cancers.

1st patient

Mrs. B . . . , aged 35 years, underwent in October 1978 a bilateral ovariectomy and a subtotal hysterectomy for a bilateral cystadenocarcinoma of the ovary. Post-operative chemotherapy (5-fluoro-uracil and endoxan) was then effected up to April 1979. At that time, she underwent a second operation with excision of the remaining cervix and omentectomy. An epiploic and ganglionary invasion was discovered. Cobalt therapy was then carried out from Nov. 5th, 1979 to Feb. 5th, 1980 on the abdomen, pelvis and diaphragm cupolas, then further chemotherapy (hexamethylmelamine) from August to October 1980. In October 1980, a voluminous oedema appeared on the whole of the left leg and an echotomograph on Oct. 27th, 1980 showed a mass of 3.5 cm at the Douglas pouch. This mass was heterogeneous, extended to the left latero-vesical; it appeared at this level to infiltrate the wall and measured 4.4 by 3 cm. Any attempt at perfusion was doomed to failure, as was a venous cut-down. Treatment by gallium chloride started on Nov. 1st, 1980 at the posology of 300 mg per day per os in three doses of 100 mg. After two months of uninterrupted treatment, clinical and biological tolerance was observed to be good. An echotomograph on Dec. 9th, 1980 showed that the mass of the Douglas pouch heterogeneous and maintained the same diameter, but the superficial mass could no longer be measured as its contours were poorly defined and in particular the vesicotumoral interface appeared to be very dense and gave a cone of attenuation to the rear indicating that the tissue of infiltration had become a sclerous tissue. A third echotomograph was made on Jan. 7th, 1981: the volume of the mass of the Douglas pouch had clearly decreased and had become oval. At the end of January 1981, the clinical state was very satisfactory and the superficial mass which could clearly be palpated in October 1980 had disappeared, so that a surgical operation could be envisaged. However, this was refused by the patient. On Mar. 20th, 1981, a pain in the left side and the epigastrium occurred suddenly with dilatation of the left colon. The treatment by gallium chloride had to be interrupted due to digestive intolerance. A sub-occlusive state was established in the days which followed, then, after a brief improvement, several sub-occlusive episodes occurred and ascites appeared. According to the surgeons, there was no possibility of surgery. The state of health worsened very quickly and death occurred on May 6th, 1981.

2nd Patient

Mr. DUP . . . Jean, aged 50 years had been attended since March 1980 for a cutaneous tumour of 3×2 cm in the left axillary region. The surgical excision made in April 1980 showed that this was a massive carcinoma occupying the dermis and hypodermis. A complete check-up to seek primary localisation was undertaken. In view of the negative nature of this check-up, the diagnosis of cutaneous primary tumour, developed at the expense of the cutaneous appendants (eccrine tumour) was retained.

The extended check-up made at the same time showed no hepatic nor pulmonary metastases. The radiographs of the bones showed a depression of the upper plate of the 12th dorsal vertebra ($D_{12}$) which was considered as metastatic all the more so as there were inflammatory type pains at this level. An irradiation of 30 $\gamma$ rays was made of $D_9$ to $C_4$ during the period of May 5th to 20th, 1980. This irradiation was completed from $D_1$ to $D_7$ by 16.5 $\gamma$ rays in three sessions from July 31st, 1980 to Aug. 4th, 1980 before the appearance of high dorsal pains and a depression of the plate of $D_6$.

Evolution was marked by the discovery at the end of July 1980 of a left axillary lymphadenopathy of 4×3 cm, of which the metastatic nature was confirmed by a surgical excision; this was a massive, ganglionary metastasis of a relatively differentiated and secreting adenocarcinoma. A cure by chemotherapy associating Adriamycine (50 mg on day 1), 5-fluoro-uracil (900 mg on days 2 and 3) and Endoxan (900 mg on day 4) was followed in this patient, who was an alcoholic, by a pancytopenia which would persist for several months and prevent this therapy from being renewed.

In April 1981, continuous, high dorsal osseous pains occurred again daily, which were not relieved by rest, with images evocative of metastasis at $D_7$ level and a clear hyperactive focus at this level, on the osseous scanner, leading to a further irradiation of 15 $\gamma$ rays of $D_1$ to $D_7$ from May 4th to 12th, 1981.

In May 1981, a new left axillary lymphadenopathy was observed, which was rounded, of 3 cm diameter. Treatment by gallium chloride started on May 20th, 1981, by the oral route, at the rate of 500 mg per day up to June 15th, 1981, then 300 mg per day from June 15th, to Aug. 18th, then 600 mg per day up to Dec. 18th, 1981, and finally, alternately, one day out of two, 600 mg and 300 mg.

The efficacity of the gallium chloride treatment was translated by the progressive regression of the lymphadenopathy from the end of July 1981. On July 23rd, 1981, the lymphadenopathy was much harder. It measured 1×1.5 cm on Nov. 12th, 1981, then 1 cm in diameter on Dec. 8th, 1981 and was no longer perceptible on Jan. 6th, 1982. On Jan. 6th, 1982, the treatment by gallium chloride was still continued and was perfectly well tolerated, without any digestive disorders or neurological, cardiac or cutaneous effects;

The general state was good, with a normal appetite, a weight of 71 kg unchanged since the beginning of the treatment;

dorsal osseous pains persisted, but of mechanical type, completely calmed by rest, with a general demineralisation of the vertebrae, perhaps a sequela to the radiotherapy;

biologically:
the inflammatory balance (haptoglobin) was normal,
the creatinine was normal: 88.50 μmol/l,
the blood cells count, hepatic balance, calcemia, phosphatemia were normal,
as for the globular Mg rates, there were between 2.80 and 3.20 mmol/l before the treatment with gallium chloride and were between 2.40 and 2.80 mmol/l in the course of treatment, which demonstrated the efficacy of the treatment. The importance of checking the globular Mg rates was furthermore clearly illustrated by the following two observations (3rd and 4th patients).

3rd patient

Mr. MOR . . . Roger, aged 73 years, underwent in April 1981 a surgical excision of a malignant melanoma of the lower left limb. This was a nodular melanoma of 1.2×1 cm, CLARK IV, with BRESLOW greater than 3 mm and an average mitotic index. There was an adjacent formation of 1.2 by 0.9 cm and 3 cutaneous metastases on the same limb. Finally, there was a massive homolateral ganglionary invasion but no controlateral invasion. No pulmonary and hepatic metastases were revealed but the prognosis was very unfavourable.

The treatment by gallium chloride was started on May 15th, 1981, at the posology of 600 mg/24 hours up to Sept. 20th, 1981, in association with a heparinotherapy at mini-doses. This heparinotherapy had been prescribed to prevent a phlebitis or pulmonary embolism following the surgical operation of April 1981 and had not been interrupted in order not to provoke the phenomenon of tumoral flare-up. [Calciparin (heparin calcium salt) 0.2 ml, 3 times per day by sub-cutaneous route]. Up to this date, the general state remained satisfactory, with a good appetite and stable weight at 70 kg. The globular magnesium rates were remarkably stable and at rates of between 2.05 and 2.30 mmol/l. On Sept. 20th, 1981, the auxiliary treatment of Calciparin was interrupted for three days for the surgical excision of a sub-cutaneous metastatic nodule on the left thigh. As we have observed on many occasions, the interruption of the Calciparin, even for a brief time, of the order of 48 hours to 72 hours, was followed very rapidly by a rapid tumoral growth not responding to any therapy. This was the case of Mr. MOR . . . Roger whose general state rapidly worsened, with appearance of a metastatic hepatomegaly of which the volume increased rapidly despite the increase in the posology of the gallium chloride to 800 mg/24 hours from Sept. 29th, 1981. This posology was tolerated up to Nov. 27th, 1981, but virtually total anorexia from this date led to the therapy being stopped. Up to Nov. 27th, 1981, the renal function and blood cells count remained normal. It was from Sept. 20th, 1981, date when the heparinotherapy was stopped, that a clear increase was observed (reaching 2.96 mmol/l on Oct. 6th, 1981) in the globular magnesium rates.

4th patient

Mr. HOT . . . Roland, aged 62 years, was operated on May 14th, 1981 for an adenocarcinoma of the colon. This was a tumour of the right angle, ulcerated and infiltrating, almost circumferential, extending over a height of 4 cm, reaching all the planes of the wall of the colon and diffusing in the adipose tissue with an attack of the ganglions of the upper right colon pedicle (with capsular excess), of two ganglions of the transverse mesocolon, a tumoral nodule within the adipose tissue of the descending nesocolon and attack of the distal small bowel. An almost total colectomy was carried out, leaving 20 cm of sigmoid and a resection of the small bowel over a length of 15 cm. The sequelas of the operation were satisfactory and treatment by gallium chloride was started, by the oral route, on May 29th, 1981 and then posology of 500 mg/24 hours, until July 1st, 1981, then continued at 300 mg/24 hours. For 4 months, the general state remained very satisfactory and the globular Mg and carcinoembryonic antigen rates remained normal. On Oct. 15th, 1981, abdominal pains were felt which gradually accentuated and the globular magnesium rates increased to 3.00 mmol/l and the carcionoembryonic antigen rates to 9 ng/ml (then to 97 ng/ml on Nov. 26th, 1981). An exploratory laparotomy was made on Nov. 12th, 1981, finding an indissectable ileomesenteric block and hepatic granulations distributed like grains of rice over the whole of the two lobes of the liver. The general state then continued to worsen, icterus appeared and death occured on Jan. 7th, 1982. With this patient, the gallium chloride therapy continued up to Nov. 10th, 1981 was insufficient at the posology of 300 ng per day to prevent a recurrence. Tolerance was perfect clinically and biologically (without renal disorders in particular) and the correlation between the clinical state, the carcinoembryonic antigen and globular magnesium rates could be emphasized.

5th patient

Mr. DRU . . . Michel, aged 68 years: the diagnosis of differenciated, mature and infiltrating epidermoid carcinoma of the oesophagus was made on Sept. 3rd, 1981. This was a voluminous tumour, extending from 23 to 32 cm, from the dental arches (according to the data from the endoscopy) with an invasion of the rear face of the origin of the left principal bronchus and the carina tracheae. In the bronchoscopy of Sept. 8th, 1981, there was a necrotic tumoral bud obstructing the light of the bronchus by two-thirds.

Gallium chloride therapy was started on Sept. 21st, 1981 at the posology of 800 mg/24 hours by the oral route.

A further bronchoscopy was made on Oct. 13th, 1981, showing the same bronchial obstruction. The existence of a considerable sub-jacent bronchial stasis and of daily dispnoeic attacks in the evening led to treatment of this bronchial tumour by laser on Oct. 20th, 1981. Following this treatment disorders in deglutition were noted and an oesobronchial fistula was demonstrated by passage to the gastrographine. Feeding by the oral route was stopped, as well as the gallium chloride treatment and, after parenteral feeding, a celestine prosthesis was positioned by endoscopic route on Nov. 3rd, 1981. The sequels of the positioning of the prosthesis was marked by the appearance of an infectious bronchial syndrome which led to death of the patient on Nov. 18th, 1981. Gallium chloride therapy could only be continued correctly for one month, but at the posology of 800 mg/24 hours and for the whole of this period, the therapy was tolerated perfectly well, both from the clinical and biological point of view, with no renal nor hepatic disturbance nor disturbances in the blood cells count.

FIGS. 1, 2 and 3 show the curves of the globular Mg (1) and plasmatic Mg (2) rates as a function of time in the course of treatment by gallium chloride (the starting point of the curves corresponding to the first administration) of the three patients. Mrs. BID . . . Marie-Francoise (1st patient, Mr. MOR . . . Roger (3rd Patient) and Mr. HOT . . . Rolan (4th patient, respectively.

These curves show that the globular magnesium rates decrease under the effect of the treatment by gallium chloride when the latter is efficacious. They rise again in the event of evolutive resumption of the tumoral process, in particular in the case of stoppage of the treatment.

To follow the globular Mg rates, the dosages must be frequent and repeated, about once a week. In fact, there are cyclic variations of the globular Mg rates with a curve of sinusoidal appearance, and the period of these cycles, like the importance of the globular Mg rates, are a function of the evolutive potential of the malignant tumour (P. COLLERY et col. "Role of Magnesium in the Development of Cancer", Trace Substances in Environmental Health, XII, 1978—A Symposium—University of Missouri—Columbia). The appearance of this curve is modified, as indicated above, by the anti-tumoral therapy by gallium chloride.

Gallium chloride may therefore constitute a drug useful in the treatment of malignant tumours, particularly of the genital tracts. It is administered by the oral route, at doses which may range from 200 mg to 1 g per day depending on the case, the treatment having to last at least two months. Checking of the globular magnesium rates may serve to judge the efficacy of the treatment and to determine the date of the end of said treatment. The active ingredient may be associated with any conventional vehicle and be packed in all forms suitable for oral administration, particularly in the form of drinkable ampoules which contain 100 to 500 mg of gallium chloride.

The composition of 10 ml ampoules, dosed at 100 mg of active ingredient, is given hereinbelow by way of example:

Gallium chloride: 0.10 g
1/5 orange concentrate: 1.875 g
Essence of mandarine: 0.125 g
Sodium methyl p-hydroxybenzoate: 0.00225 g
Sodium propyl p-hydroxybenzoate: 0.00025 g
Granulated sugar: 2 g
Distilled water qsp 10 ml.

What is claimed is:

1. A method for the treatment of malignant tumors in a human comprising administering to said human by the oral route from 200 mg. to 1 g/day of gallium chloride, for at least two months.

2. A method according to claim 1 wherein the gallium chloride is administered in the form of a drinkable ampoule.

* * * * *